(12) United States Patent
Pensak, Jr. et al.

(10) Patent No.: US 7,917,250 B2
(45) Date of Patent: Mar. 29, 2011

(54) DEVICES, SYSTEMS AND METHODS FOR FLOW-COMPENSATING PUMP-INJECTOR SYNCHRONIZATION

(75) Inventors: Stanley P. Pensak, Jr., East Walpole, MA (US); John Heden, Hollis, NH (US); Steven J. Ciavarini, Natick, MA (US); John Lamoureux, Franklin, MA (US); Miguel Soares, Norton, MA (US)

(73) Assignee: Waters Technologies Corporation, Milford, MA (US)

( * ) Notice: Subject to any disclaimer, the term of this patent is extended or adjusted under 35 U.S.C. 154(b) by 481 days.

(21) Appl. No.: 11/658,985

(22) PCT Filed: Aug. 19, 2005

(86) PCT No.: PCT/US2005/029734
§ 371 (c)(1),
(2), (4) Date: Oct. 3, 2008

(87) PCT Pub. No.: WO2006/023828
PCT Pub. Date: Mar. 2, 2006

(65) Prior Publication Data
US 2009/0062966 A1    Mar. 5, 2009

Related U.S. Application Data

(60) Provisional application No. 60/604,373, filed on Aug. 24, 2004.

(51) Int. Cl.
| | | |
|---|---|---|
| G05D 11/02 | (2006.01) | |
| G05D 11/16 | (2006.01) | |
| G05B 21/00 | (2006.01) | |
| G01F 1/00 | (2006.01) | |
| G01F 7/00 | (2006.01) | |
| G01F 25/00 | (2006.01) | |
| F01N 3/20 | (2006.01) | |
| G05B 1/00 | (2006.01) | |

(52) U.S. Cl. .......... 700/285; 700/265; 700/282; 702/45; 702/46; 702/47; 73/1.35; 73/61.56; 378/47; 378/80; 378/83; 422/105; 210/198.1; 210/198.2

(58) Field of Classification Search .................. 700/265, 700/282, 285; 702/45–47; 73/1.35, 61.56; 378/47, 80, 83; 422/100–101, 105; 210/198.1, 210/198.2
See application file for complete search history.

(56) References Cited

U.S. PATENT DOCUMENTS

| | | | | |
|---|---|---|---|---|
| 3,985,021 | A * | 10/1976 | Achener et al. | 73/61.56 |
| 5,954,954 | A * | 9/1999 | Houck et al. | 210/198.2 |
| 6,592,822 | B1 * | 7/2003 | Chandler | 422/82.05 |
| 7,267,798 | B2 * | 9/2007 | Chandler | 422/82.05 |
| 7,384,605 | B2 * | 6/2008 | Feldstein | 422/100 |
| 2002/0017484 | A1 * | 2/2002 | Dourdeville | 210/198.2 |
| 2005/0008516 | A1 * | 1/2005 | Richardson et al. | 417/540 |
| 2005/0142662 | A1 * | 6/2005 | Bonne | 436/149 |
| 2006/0121624 | A1 * | 6/2006 | Huang et al. | 436/180 |
| 2007/0281288 | A1 * | 12/2007 | Belkin et al. | 435/4 |
| 2008/0164155 | A1 * | 7/2008 | Pease et al. | 205/777.5 |

* cited by examiner

*Primary Examiner* — Ramesh B Patel
(74) *Attorney, Agent, or Firm* — Edwards Angell Palmer & Dodge LLP; Peter C. Lauro, Esq.; George N. Chaclas, Esq.

(57) ABSTRACT

Systems, devices, and methods to mitigate the pressure disturbance associated with the injection of low-pressure analyte samples into a high-pressure HPLC fluid stream to enhance chromatographic performance related to retention time and reproducibility. The injection event is coordinated with active pressure control of a binary solvent delivery system to virtually eliminate the customary pressure drop when the low-pressure loop is brought on line. Consistent timing with the injection event of the mechanical position of the delivery pump pistons, and the start and subsequent gradient delivery generates reproducible results.

39 Claims, 7 Drawing Sheets

DEVICES, SYSTEMS AND METHODS FOR FLOW-COMPENSATING PUMP-INJECTOR SYNCHRONIZATION

CROSS-REFERENCE TO RELATED APPLICATIONS

This application is a U.S. national phase application, pursuant to 35 U.S.C. §371, of PCT international application Ser. No. PCT/US2005/029734, filed Aug. 19, 2005, designating the United States and published in English on Mar. 2, 2006 as publication WO 2006/023828 A2, which claims priority to U.S. Provisional Application Ser. No. 60/604,373, filed Aug. 24, 2004. The entire contents of the aforementioned patent applications are incorporated herein by this reference.

BACKGROUND OF THE INVENTION

1. Field of the Invention

The present invention relates to high-performance liquid chromatography ("HPLC") and, more particularly, to devices, systems, and methods for controlling a plurality of pumps that are injecting analyte samples into an HPLC fluid stream by synchronizing their pump cycle and the switch time of injection.

2. Background Art

Scientific laboratories commonly need to separate chemical compounds on such basis as the compound's molecular weight, size, charge or solubility. Separation of the compounds is often a first step in the identification, purification, and quantification of the compounds. Chromatography or, more specifically, high performance liquid chromatography ("HPLC") has become the analytical tool of choice for applications as varied as biotechnological, biomedical, and biochemical research as well as for the pharmaceutical, cosmetics, energy, food, and environmental industries.

As advances in technology emerge, manufacturers of HPLC instruments are quick to improve the performance of their product lines. In fact, improvements in one technological area or subsystem typically spurn on advancement in interrelated areas or subsystems. For example, U.S. Pat. No. 6,147,595 to Staal, which is incorporated in its entirety herein by reference, discusses several advantages and disadvantages related to evolving approaches based on new technology.

Currently, there are several pump types commonly used as subsystems with HPLC instruments. For example, HPLC instruments may incorporate reciprocating pumps, syringe pumps, and constant pressure pumps, all of which are known to those of ordinary skill in the art.

Most reciprocating pumps include a small, motor-driven plunger that moves rapidly back and forth in a hydraulic chamber to vary the chamber volume. On the backstroke, the plunger creates a negative pressure that pulls in a solvent and on the forward stroke, the plunger of the reciprocating pump pushes the solvent out to a column. In order to achieve steady flow rate to the column, multiple plungers are employed. The multiple plungers may be employed in series or in parallel to achieve the desired delivery flow and pressure.

During compression of the solvent, however, in the pump chamber, energy is absorbed locally that raises the temperature of the solvent. The localized, thermal effect is proportional to the solvent compressibility, its specific heat, the target pressure, e.g., the desired instrument operating pressure, and the rate at which the solvent is compressed. For many leading edge technology HPLC instruments, high pressure and the limited amount of time to compress the solvent create further adverse localized thermal effects in the pump chamber and elsewhere. For example, heat imparted to the solvent produced by compression is usually dissipated to the surroundings, e.g., pump head ambient temperature, at a rate dependent upon the relative mass and thermal conductivity of the compressed solvent and the surroundings.

In most applications and pressures of up to a couple thousand pounds per square inch ("psi"), the thermal effects of compression are negligible. However, at higher pressures, the thermal effects—especially the localized thermal effects—become more appreciable. Moreover, these thermal effects create errors in the pressure of the compressed solvent because the solvent temperature is elevated during compression compared with its delivery during analysis in the instrument. In other words, once the solvent is compressed to a target pressure, the pressure decays as the solvent temperature moves toward equilibrium with the temperature of the instrument. As a result, typically, the compressed solvent settles to a pressure below the target operating pressure and, thereby, creates a deficit in delivered flow.

Prior art pump control systems lack the required ability to react to the localized thermal effects of solvent compression at higher pressures. So despite the advances of the state of the art, HPLC instruments are lacking in stability and performance. As a result, inaccurate results are still common.

Recognizing the shortcomings of the prior art, a high-pressure serial pump was disclosed in U.S. Provisional Patent Application No. 60/587,381 for a "High Pressure Pump Controller" that was filed on Jul. 13, 2004 and is incorporated herein by reference. High-pressure pumps for use in chromatography applications normally use a reciprocating-type design involving two pistons that operate in corresponding chambers. Depending on the fluidic configuration, there are two main design types: parallel or series. In a parallel design, the two pistons alternate in operation whereby one piston delivers flow while the other intakes new solvent from the solvent source and vice versa. In contrast, with a series design, typically one piston, i.e., the primary piston, intakes solvent from the solvent source and delivers the solvent to the other piston. The other piston, i.e., the accumulator piston, performs most of the solvent delivery to the system. In short, the primary piston refills the accumulator piston rapidly at high pressure when, inevitably, the accumulator piston needs to intake new solvent.

Referring to FIG. 1, a series-type reciprocating pump of a type well-known to the art will be described. A primary pumping actuator 12 comprises a primary chamber 12a with a reciprocating primary piston 12b, which terms will be used interchangeably throughout this specification unless otherwise noted. Similarly, the accumulator pumping actuator 14 comprises an accumulator chamber 14a with a reciprocating accumulator piston 14b, which terms, likewise, will be used interchangeably throughout this specification unless otherwise noted.

The primary piston 12b intakes solvent from the solvent source 18, e.g., by creating a negative pressure, and delivers the solvent to both the accumulator chamber 14a of the accumulator pumping actuator 14 and to the system 15. After solvent is delivered from the primary pumping actuator 12 to the accumulator pumping actuator 14, the reciprocating accumulator piston 14b is at or near the end of its backstroke. When the reciprocating accumulator piston 14b begins its forward stroke, the reciprocating accumulator piston 14b introduces the solvent to the system 15. Check valves 11 and 13 allow fluid, i.e., solvent, to pass in one direction only. As a result, solvent in the primary chamber 12a cannot drain back into the solvent source 18 and solvent in the accumulator chamber 14a cannot drain back into the primary chamber 12a. Respective pressure transducers 17 and 19 measure pressure at the outlet of each chamber 12a and 14a, respectively.

Typically, while the accumulator piston 14b delivers flow to the system 15 at high pressure, the primary piston 12b intakes new solvent from the solvent source 18 and waits until it is time to refill the accumulator chamber 14a before starting its forward stroke. Immediately prior to the time when the accumulator chamber 14a requires refilling, the primary piston 12b begins its forward stroke to compress the solvent. Preferably, the primary piston 12b compresses the solvent to the same or substantially the same solvent pressure that is measured by the accumulator transducer 19, i.e., the system pressure, and is set ready for delivering its solvent to the accumulator chamber 14a. Thus, when the accumulator piston 14b approaches the end of its delivering motion (or stroke), the pump controller (not shown) signals the primary piston 12b to deliver solvent and the accumulator chamber 14a to intake solvent. This operation, known as "transfer" is performed rapidly at high pressure and at a high flow rate and continues until the primary piston 12b completely delivers its compressed solvent to the accumulator chamber 14a and to the system 15 while the accumulator piston 14b is re-filled with solvent and ready to resume its normal delivery.

During transfer operation, while the accumulator piston 14b is intaking solvent from the primary pumping actuator 12, the accumulator piston 14b, obviously, cannot also deliver solvent to the system 15. As a result, to avoid interruption in the flow delivered to the system 15, the primary piston 12b becomes responsible for delivering solvent to the system 15, in addition to re-charging the accumulator chamber 14a. To accomplish this task, necessarily, transfer is performed by the primary piston 12b at a higher plunger velocity so that, in addition to completely delivering compressed solvent to the accumulator chamber 14a, a portion of the solvent is delivered to the system 15. To provide the necessary pressure to serve both the accumulator chamber 14a and the system 15, the primary piston 12a plunger velocity must be greater than the accumulator piston's normal delivery velocity. This is referred to as "over-delivery", which is the difference between the higher plunger velocity and the normal delivery velocity.

Once the transfer operation is finished, the pump controller signals the accumulator piston 14b to resume normal flow delivery and the primary piston 12b to intake new solvent. This cycle, known as the "pump cycle", is repeated continuously while the accumulator piston 14b is delivering solvent to the system 15. Pump cycle duration depends mainly on the stroke volume of the primary piston 12b and the delivered flow rate.

The role of the check valves 11 and 13 is easy to understand. The primary check valve 11 allows the primary piston 12b to intake solvent at atmospheric pressure from the solvent source 18, and, further, prevents the solvent from flowing back to the solvent source 18 during compression and delivery. Similarly, the accumulator check valve 13 allows the primary piston 12b to deliver solvent to the accumulator chamber 14a, and, further, prevents compressed solvent from flowing back to the primary chamber 12a when the accumulator piston 14b delivers solvent to the system 15 at high pressure and/or when the primary piston 12b intakes new solvent at atmospheric pressure.

The accumulator pressure transducer 19 measures system pressure and provides the pressure input to a pressure control algorithm (not shown). The accumulator pressure transducer 19 also provides the target operating pressure for the primary piston 12b when the primary piston 12b starts the compression, i.e., forward stroke, of new solvent. The primary pressure transducer 17 measures the pressure inside the primary chamber 12a, so that the stroke of the primary piston 12b is stopped when the pressure reaches the target operating pressure.

Generally, with HPLC, bringing an un-pressurized or relatively low-pressurized sample loop on line causes a significant pressure drop to the system 15. The pressure drop is further worsened when the analyte sample is aspirated into the fluid stream of the sample loop with air gaps to mitigate dispersion of the sample.

Indeed, when the solvent inside the primary piston 12b is compressed, its temperature rises. This temperature increase is referred to as "adiabatic heating" and is eventually lost to the solvent surroundings and to the system 15 (when the primary piston 12b starts delivering to the accumulator chamber 14a and/or the system 15), at a rate dependent on the relative mass and thermal conductivity of the compressed solvent and its surroundings. However, this temperature loss creates an error in the pressure of the compressed solvent, because the solvent temperature and pressure at the time of compression are higher than the temperature and pressure that the solvent will eventually have, i.e., the operating temperature and operating pressure of the system 15.

Therefore, once the solvent is compressed to the target pressure, i.e., system operating pressure, its pressure starts to decay as its increased temperature starts to equilibrate back down to system operating temperature. The compressed solvent pressure eventually settles at a value below the intended system operating pressure, which creates a deficit in delivered flow when the primary piston 12b starts delivering, i.e., "over-delivering" to the system 15. The thermal effect is proportional to the solvent compressibility, to the specific heat of the solvent, to the compression pressure, and to the rate at which the solvent is compressed.

As stated previously, for pressures up to a few thousand psi, this thermal effect can normally be ignored. However, at higher pressures, the thermal effect can be more significant. Furthermore, due to the precision timing involved and required in the reciprocating pumps' action, there is normally a limited amount of time to compress the solvent from atmospheric pressure to system operating pressure. Therefore, this thermal effect creates significant flow delivering errors, which represent solvent composition errors when the solvents of two or more pumps are combined together at high pressure to form a solvent gradient.

Furthermore, when the outlets of two or more parallel pumps delivering dissimilar solvents are connected together to a common fluid node, it becomes necessary to prevent the control loops from interacting or oscillating when the control periods, which is to say the transfer operation periods, of the pumps overlap, or "collide".

Isolation restrictors have been proposed to isolate the control loops from external fluid conditions. However, this isolation is not enough for high-precision solvent gradients, where the small remaining interaction between both pump's control loops creates solvent composition errors, i.e., "collisions".

To eliminate these errors and avoid collisions, it would be desirable to provide devices, systems, and methods that enable the two pumps to interchange information about their respective position within the pump cycle to avoid their control periods overlapping. Thus, when a control period "collision" is foreseen, the pump with a longer pump cycle advances its control period just enough to avoid the overlap with the other pump control period. This technique effectively removes any remaining composition errors in solvent gradients and avoids "collisions".

Also, it would be desirable to provide control devices, control systems, and control methods to mitigate pressure disturbance that is associated with injection of lower pressure analyte samples into a higher pressure HPLC fluid stream. It would also be desirable to provide control devices, control systems, and control methods to enhance chromatographic performance related to retention time and area reproducibility. It would further be desirable to provide control devices, control systems, and methods to enhance reproducibility of results by forcing a consistent timing relationship between the injection event of the analyte sample, the mechanical position of the pumps' plungers, and the start and subsequent solvent gradient of the analyte sample delivery.

SUMMARY OF THE INVENTION

In its broadest terms, the present invention provides systems, devices, and methods to mitigate the pressure disturbance associated with the injection of analyte samples at or near atmospheric pressure into a higher-pressure HPLC fluid stream, and to enhance chromatographic performance related to retention times and area (of the elution peaks) reproducibility. The preferred embodiments coordinate the injection event with the active pressure control of a binary solvent delivery system to virtually eliminate the customary pressure drop when the lower-pressure loop containing the analyte sample is brought on line. An additional benefit that enhances reproducibility is accomplished by forcing a consistent timing relationship between the injection event, the mechanical position of the delivery pump pistons, and the start of the subsequent gradient delivery.

In a first embodiment, the present invention provides a device for controlling introduction of an analyte sample at a first pressure into a fluid stream at a higher second pressure, wherein the fluid stream is that of a system for analyzing the analyte sample, and introduction occurs during a forced transfer operation involving a plurality of pumping actuators having one dominant flow pumping actuator and at least one non-dominant flow pumping actuator, to minimize an expectant pressure drop that occurs when the analyte sample is introduced into said fluid stream. Preferably, the device comprises a first signaling means for providing a first signal to the plurality of pumping actuators; memory for storing a pre-determined injector pre-inject time delay and a pre-determined pump time delay; a time-measuring means for measuring a first amount of time after the first signal and a second amount of time after the first signal; a comparator for comparing the first and second amounts of time, respectively, to the pre-determined injector pre-inject time delay and the pre-determined pump time delay stored in memory; a second signaling means for providing a second signal to the dominant pumping actuator of the plurality of pumping actuators when the second amount of time equals the pre-determined pump time delay; and a third signaling means for providing a third signal to an injector valve through which the analyte sample is introduced into the fluid stream of the system when the first amount of time equals the pre-determined injector pre-inject time delay. More preferably, the first signal causes the dominant flow pumping actuator and the non-dominant flow pumping actuator to perform a first forced transfer operation concurrently. Still more preferably, the second signal causes only the dominant flow pumping actuator to perform a second forced transfer operation.

In one aspect of the first embodiment, the device further comprises means to synchronize the mechanical phase of each pumping actuator with at least one of an injection sequence and a start of a gradient run to enhance retention time reproducibility between a plurality of injection runs.

In another aspect of the first embodiment, the second forced transfer operation overlaps an injection event occurring when the analyte sample is introduced into the fluid stream of the system. More preferably, the device is structured and arranged to provide active pressure control during each forced transfer operation to minimize disturbance in the fluid stream during introduction of the analyte sample.

In a second embodiment, the present invention provides a piece of software for controlling introduction of an analyte sample at a first pressure into a fluid stream at a higher second pressure, wherein the fluid stream is that of a system for analyzing the analyte sample, during a forced transfer operation involving a plurality of pumping actuators having one dominant flow pumping actuators and at least one non-dominant flow pumping actuator, to minimize an expectant pressure drop that occurs when the analyte sample is introduced into the fluid stream. Preferably, the piece of software has an algorithm that comprises providing a first signal to a plurality of pumps; storing a pre-determined injector pre-inject time delay and a pre-determined pump time delay in memory; measuring a first amount time after the first signal and a second amount of time after the first signal; comparing the first and second amounts of time, respectively, to the pre-determined injector pre-inject time delay and the pre-determined pump time delay stored in memory; providing a second signal to the dominant flow pumping actuator of the plurality of pumping actuators when the second amount of time equals the pre-determined pump time delay; and providing a third signal to an injector valve through which the analyte sample is introduced into the fluid stream of the system, for analyzing said analyte sample, when the first amount of time equals the pre-determined injector pre-inject time delay.

Preferably, the algorithm ensures that the second forced transfer operation overlaps an injection event occurring when the analyte sample is introduced into the fluid stream of the system. More preferably, the algorithm provides active pressure control during at least one forced transfer operation during the injection event to minimize disturbance in the fluid stream. Still more preferably, the software algorithm further includes synchronizing the mechanical phase of each pumping actuator with at least one of an injection sequence and a start of a gradient run to enhance retention time reproducibility between a plurality of injection runs.

In a third embodiment, the present invention provides a system for controlling introduction of an analyte sample at a first pressure during active pressure control of a dominant flow pumping actuator, to minimize an expectant pressure drop that occurs when the analyte sample is introduced into a fluid stream of a system for analyzing said analyte sample. Preferably, the control system comprises a control device for receiving pressure measurements and for providing signals for active pressure control; a plurality of pumping actuators to provide high-pressure mixing of gradients of a plurality of solvents into a fluid stream of the system for analyzing the analyte sample, wherein each of the plurality of pumping actuators is in fluid communication with a flow-combining device, and wherein a dominant flow pumping actuator that is further in fluid communication with a first solvent source; and one or more non-dominant flow pumping actuators that are further in fluid communication with a one or more solvent sources; and an autosampler that is structured and arranged at an injector, to provide signals to the control device.

Preferably, the dominant flow pumping actuator and one or more non-dominant flow pumping actuators include a primary pumping actuator having a chamber and a piston that is disposed downstream of and in fluid communication with a solvent source; and an accumulator pumping actuator having a chamber and a piston that is disposed downstream of and in series with the primary pumping actuator and upstream of an injector.

In one aspect of the third embodiment, the system further includes a check valve that is disposed between the primary pumping actuator and the solvent source, wherein in an open position, the check valve provides fluid communication between the primary pumping actuator and the solvent source so that the piston can intake solvent from the solvent source and store said solvent in the chamber, and in a closed position, the check valve isolates the primary pumping actuator from the solvent source to prevent solvent in said chamber from flowing back into said solvent source when the piston of said primary pumping actuator compresses said solvent in said chamber or delivers said solvent to the chamber of the accumulator pumping actuator. Preferably, the system further includes a check valve that is disposed between the primary pumping actuator and the accumulator pumping actuator, wherein in an open position, the check valve provides fluid communication between the chamber of the primary pumping actuator and the chamber of the accumulator pumping actuator so that the piston of the primary pumping actuator can deliver solvent to said chamber of said accumulator pumping actuator, and, in a closed position, the check valve isolates the chamber of the accumulator pumping actuator from the primary pumping actuator to prevent solvent in said chamber of said accumulator pumping actuator from flowing back into the chamber of said primary pumping actuator when the piston of said accumulator pumping actuator compresses the solvent in said accumulator chamber or delivers said solvent to the system.

In another aspect of the present invention, the system is structured and arranged so that during the first forced transfer operations, the primary pistons of the dominant flow pumping actuator and the non-dominant flow pumping actuator compress their aspirated solvent; re-fill their associated accumulator chambers; and, further, deliver compressed solvent to the injector. More preferably, the system is structured and arranged so that during a second forced transfer operation, the primary piston of the dominant flow pumping actuator compresses its aspirated solvent; re-fills its associated accumulator chamber; and, further, delivers compressed solvent to the injector.

In yet another aspect of the third embodiment, the system is structured and arranged so that active pressure control ensures that there is no overlap between a control period of the dominant flow pumping actuator and a control period of the non-dominant pump during a second forced transfer operation. Preferably after the second forced transfer operation, during the run, the overlap between the control periods of the dominant flow pumping actuator and the non-dominant flow pumping actuator is avoided by advancing the control period of one of said pumping actuators having the longer pump cycle than the other of said pumping actuators. More preferably, during active pressure control, the dominant flow pumping actuator provides a greater share of solvent at the starting condition of a system run. Still more preferably, the dominant flow pumping actuator provides either an aqueous solvent (reverse phase chromatography) or a solvent that is weaker that the solvent provided by the non-dominant flow pumping actuator.

In still another aspect of the third embodiment, the autosampler provides a first signal to the control device to initiate the first forced transfer operation. Preferably, the autosampler provides the first signal to the control device at some pre-determined, fixed time period prior to activating the injector, to enable pump synchronization. More preferably, the autosampler provides a second signal to the control device to initiate the second forced transfer operation. Still more preferably, the autosampler provides the second signal to the control device at some pre-determined, fixed time period prior to activating the injector to enable pump synchronization.

In a fourth embodiment, the present invention provides a method of providing active pressure control to a system for controlling introduction of an analyte sample at a first pressure into a solvent fluid stream at a higher pressure from one of a plurality of pumping actuators to minimize an expectant pressure drop that occurs when the analyte sample at a lower pressure is introduced into a system for analyzing said analyte sample. Preferably, the method comprises preparing the analyte sample for introduction into the fluid stream; initiating a first forced transfer operation, wherein the first forced transfer operation includes at least one of synchronizing the delivery stroke of a plurality of accumulator actuator pistons among the plurality of pumping actuators, thus synchronizing the mechanical phase of the plurality of accumulator actuator pistons during the subsequent run; initiating a second forced transfer operation, wherein the second forced transfer operation is applied only to the dominant flow pumping actuator while the non-dominant primary pumping actuator is in its rest state; and activating an injector valve to introduce said analyte sample into the fluid stream of the system.

Preferably, the first forced transfer operation is initiated at a first, pre-determined, fixed time delay prior to activating the injector valve. More preferably, the first forced transfer operation is initiated prior to the injection event to synchronize the dominant flow pumping actuator with the non-dominant flow pumping actuator. Still more preferably, the step of initiating a second forced transfer operation overlaps the step of activating the injector valve to introduce the analyte sample into the fluid stream of the system.

In a fifth embodiment, the present invention provides a device for controlling introduction of an analyte sample at a first pressure into a fluid stream at a higher second pressure, wherein the fluid stream is that of a system for analyzing the analyte sample, during a forced transfer operation involving a plurality of pumping actuators having one dominant flow pumping actuator and at least one non-dominant flow pumping actuator, to minimize an expectant pressure drop that occurs when the analyte sample is introduced into the fluid stream of the system. Preferably, the device comprises memory for storing a pre-determined injector pre-inject time delay and a pre-determined pump time delay; a time-measuring means for measuring a first amount of time after a first signal and a second amount of time after the first signal; a comparator for comparing the first and second amounts of time, respectively, to the pre-determined injector pre-inject time delay and the pre-determined pump time delay stored in memory; and a controller.

More preferably, the controller provides the first signal to the plurality of pumps; provides a second signal to the dominant pump of the plurality of pumps when the second amount of time equals the pre-determined pump time delay; and provides a third signal to an injector valve through which the analyte sample is introduced into the fluid stream of the system when the first amount of time equals the pre-determined injector pre-inject time delay.

In one aspect of the fifth embodiment, preferably, the first signal causes the dominant flow pumping actuator and the non-dominant flow pumping actuator to perform a first forced transfer operation concurrently. More preferably, the second signal causes only the dominant flow pumping actuator to perform a second forced transfer operation. Still more preferably, the device further comprises means to synchronize the mechanical phase of each pumping actuator with at least one of an injection sequence and a start of a gradient run to enhance retention time reproducibility between a plurality of injection runs.

In another aspect of the fifth embodiment, the second forced transfer operation overlaps an injection event occurring when the analyte sample is introduced into the fluid stream of the system. Preferably, the device is structured and arranged to provide active pressure control during each forced transfer operation to minimize disturbance in the fluid stream during introduction of the analyte sample into the fluid stream.

BRIEF DESCRIPTION OF THE DRAWINGS

The invention will be better understood by reference to the following more detailed description and accompanying drawings where like reference numbers refer to like parts.

DETAILED DESCRIPTION OF THE INVENTION AND CERTAIN EMBODIMENTS THEREOF

Figure 1:
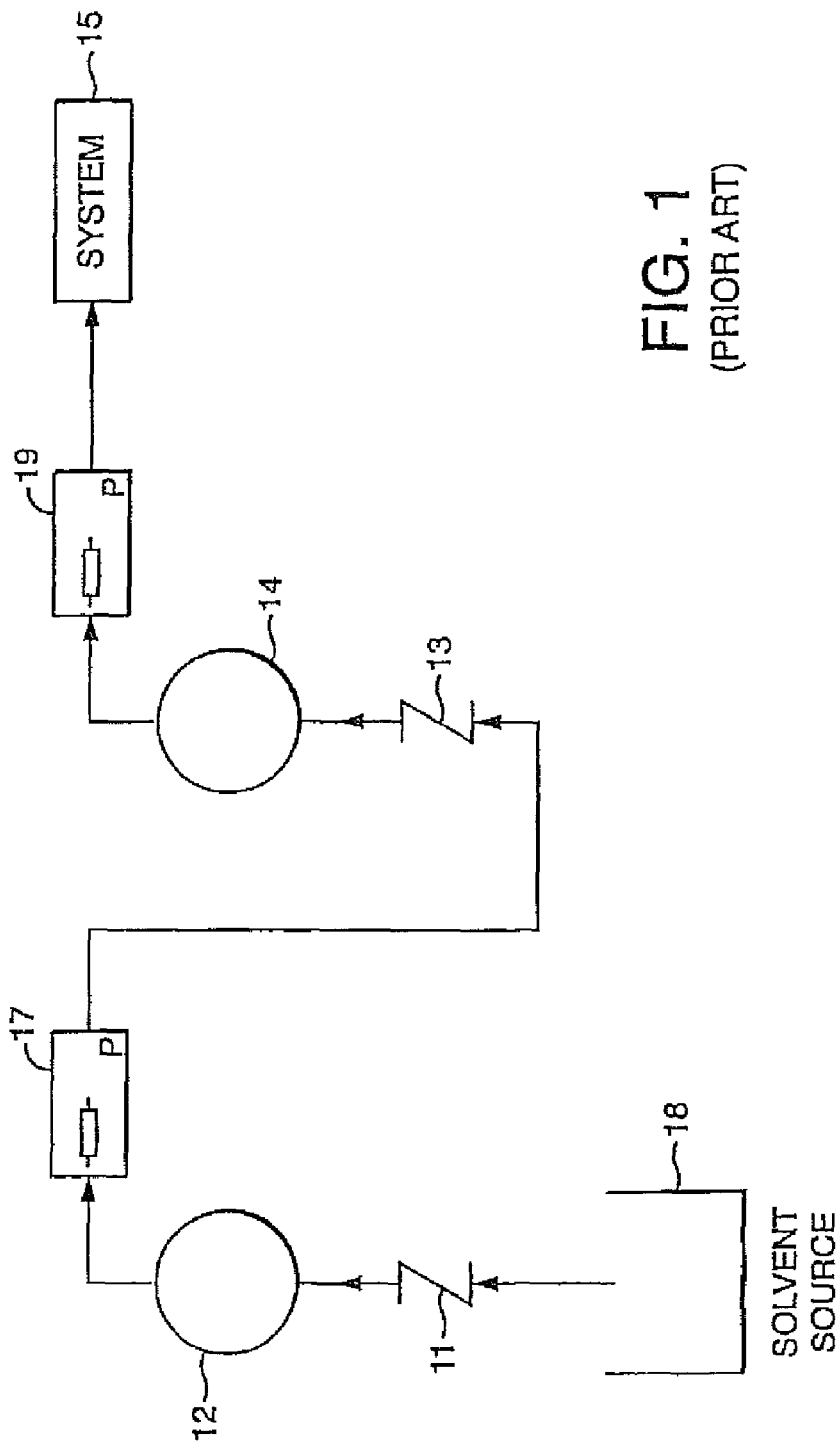
FIG. 1 is a representative embodiment of a high-pressure serial pump in accordance with the prior art.
Figure 2:
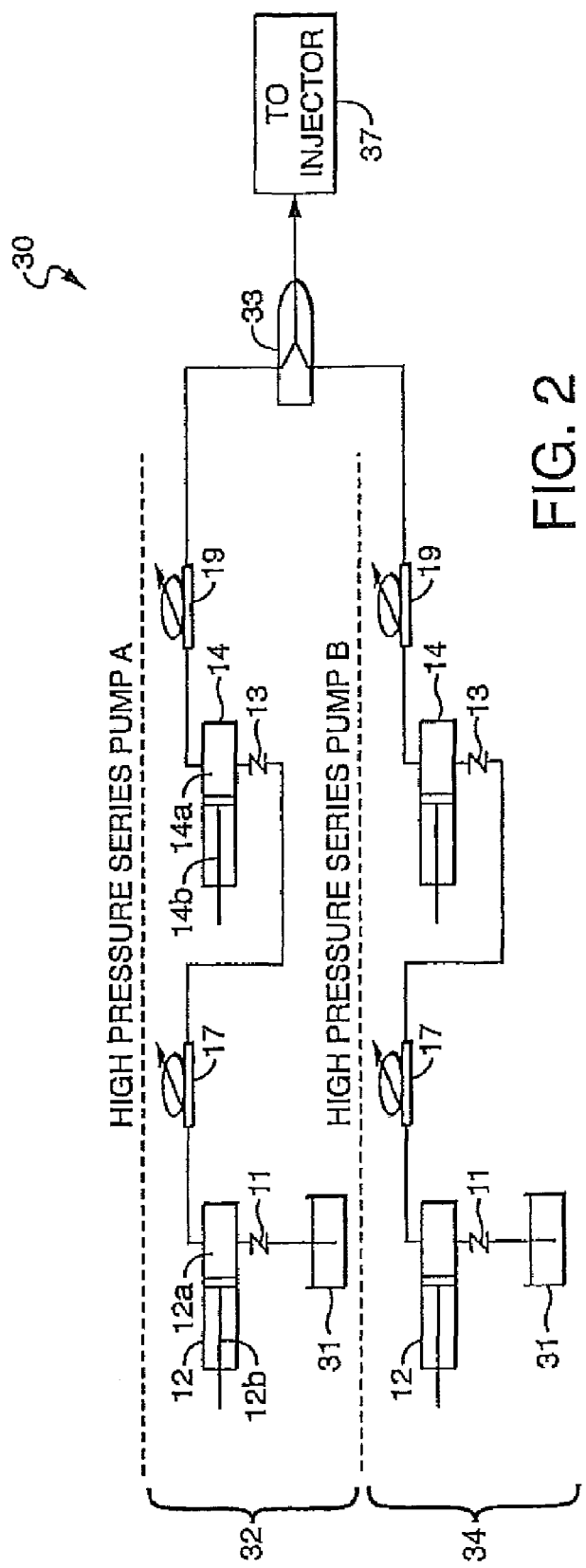
FIG. 2 is an illustrative embodiment of a binary solvent delivery system ("SDS") in accordance with the present invention.
Figure 5:
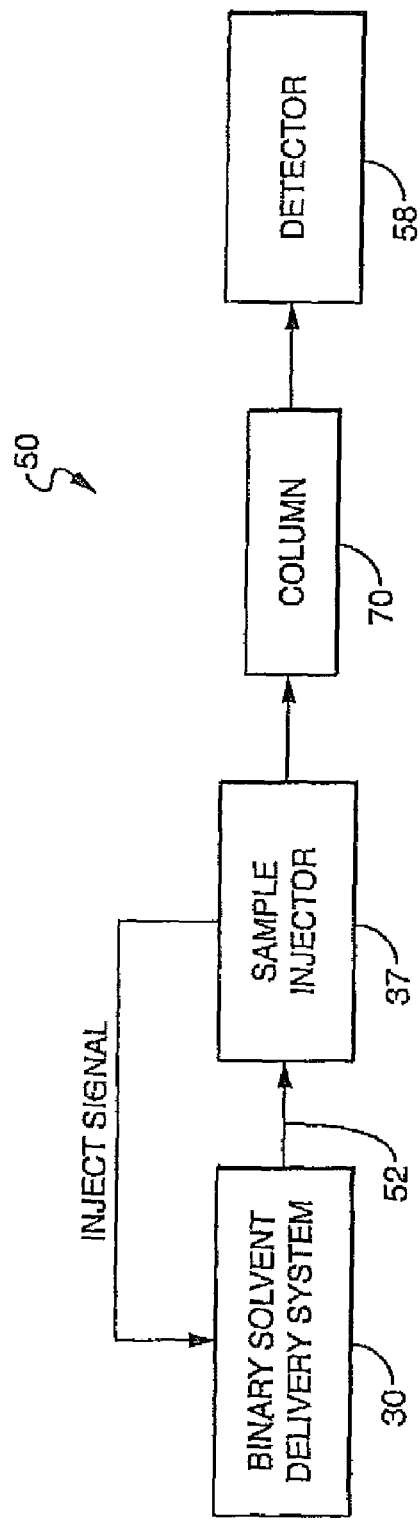
FIG. 5 is an illustrative embodiment of an SDS and an autosampler injector in accordance with the present invention.

FIG. 2 shows embodiments of an HPLC, binary solvent delivery system ("SDS") 30 in accordance with the present invention. FIG. 5, further, shows an embodiment of an SDS 30 in operational association with an autosample injector 37, a system column 70, and a system for analyzing an analyte sample 58.

As the name suggests, the SDS 30 comprises a plurality of pumping actuators, e.g., pumps 32 and 34 that provide high-pressure mixing of two or more solvents, e.g., a first solvent and a second solvent, and introduces those solvents in some proportion into the fluid stream 52 of the SDS 30. Preferably, the outlets of each of the pumps 32 and 34 are connected at the same or substantially the same mechanical location via a flow-combining device 33, e.g., a T-section. More preferably, the outlets of each of the pumps 32 and 34 are in proximity of the autosample injector 37, to minimize system delay volume. In an alternate embodiment, the pumps 32 and 34 could also be connected to the fluid stream 52 of the SDS 30 via a mixer (not shown) to augment blending of the proportioning solvents prior to introduction into the fluid stream 52 instead of a T-section 33.

Figure 6:
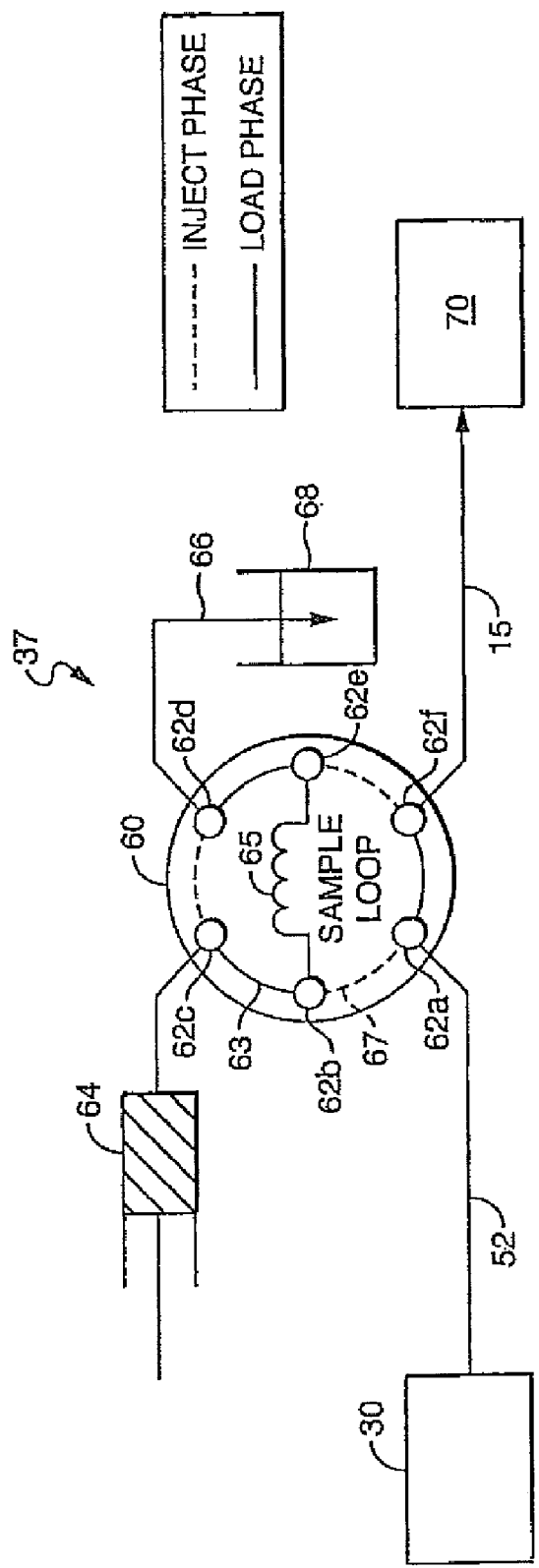
FIG. 6 is an illustrative embodiment of an autosampler injector in accordance with the present invention.

The SDS 30 provides a mixture of a plurality of higher-pressure solvents to the autosample injector 37. Depending on its operations state, the autosample injector 37 will either transmit the mixture of solvents to the column 70 directly or, alternatively, will introduce an analyte sample into the mixture of solvents and then introduce this mixture of solvents and analyte sample to the column 70. Preferably, the analyte sample, which, typically, is at or near atmospheric pressure, is combined with the plurality of solvents. More preferably, the pressure of the solvents and analyte sample is increased to be compatible with the system operating pressure in the column 70. Referring to FIG. 6, a preferred embodiment of an autosample injector (the "injector") 37 and its operational relationship with the SDS 30 and the rest of the system comprising the column 70 and the detector 58 will now be described.

Preferably, the injector 37 comprises a multi-port, multi-position, rotary valve 60 of a type that is well known to those skilled in the art. More preferably, the injector 37 is a six-port, two-position rotary valve 60. Each of the ports $62a$-$62f$ provides internal and external fluidic communication between one of the rotary valve 60, the fluid stream 52 of the SDS 30, the column 70, a low-pressure drawing syringe (or "piston") 64, and an injector needle 66.

For example, as shown in FIG. 6, the fluid stream 52 of the SDS 30 can be in fluidic communication with port $62a$; the drawing syringe 64 can be in fluidic communication with port $62c$; the injector needle 66 can be in fluidic communication with port $62d$; the column 70 can be in fluidic communication with port $62f$; and ports $62b$ and $62e$ can be in fluidic communication with each other to provide a "sample loop" 65. Fluidic communication between adjacent ports 62 (except ports $62b$ and $62e$ in the "sample loop" 65) depends on the operating state of the injector 37.

The autosample injector 37 operates in one of two states, which is to say, a load state and an injection state. During or as part of the load state, the rotary valve 60 is configured to establish direct fluidic communication between port $62a$ and port $62f$, between port $62b$ and port $62c$, and between port $62d$ and port $62e$. These connections are depicted in FIG. 6 as solid lines 63. Accordingly, during or as part of the load state, the higher-pressure fluid stream 52 from the SDS 30 can flow directly through the rotary valve 60, i.e., between port $62a$ and port $62f$, to the column 70.

Additionally, during or as part of the load state, the drawing syringe 64 and analyte sample source 68 are in fluidic communication via the sample loop 65 and the injector needle 66. Thus, the drawing syringe 64 can aspirate a desired volume of analyte sample from the sample source 68, i.e., the sample vial, and draw a desired volume of analyte sample into the sample loop 65, where it can remain in an at-rest condition and at atmospheric pressure until it is time to inject the analyte sample into the fluid stream 52 of the SDS 30 for delivery to the column 70. Air gaps (not shown) can also be introduced into the sample loop 65 during aspiration, to mitigate loss of analyte sample in the needle transport line between the injector needle 66 and the rotary valve 60 and in the fluid lines 63 and 67.

During the second, injection state, the rotary valve 60 establishes direct fluidic communication between port $62a$ and port $62b$, between port $62c$ and port $62d$, and between port $62e$ and port $62f$. These connections are depicted in FIG. 6 as dotted or dashed lines 67. Accordingly, during or as part of the injection state, the at-rest analyte sample in the unpressurized sample loop 65 is placed in direct fluidic communication with the higher-pressure fluid stream 52 of the SDS 30 and with the separation column 70. The drawing syringe 64 and injector needle 66 are no longer in communication with, i.e., are isolated from, the sample loop 65.

During the injection stage in which the analyte sample, resting in sample loop 65 at or near atmospheric pressure, is introduced quickly into the high-pressure fluid stream 52 in the rotary valve 60, the pressure of the fluid stream 52 falls precipitously. As a result, the driving flow through the column 70 is interrupted, thus greatly affecting chromatographic performance at the start of the gradient. Consequently, to compensate for the pressure drop and to minimize the loss of flow, the fluid (and air gaps) in the sample loop 65 is advantageously compressed rapidly to conform to the pressure of the column 70, i.e., the system operating pressure.

The injection event, therefore, is advantageously coordinated, e.g., using active pressure control of the SDS 30, to virtually eliminate the customary pressure drop when the low-pressure loop is brought on line. Specifically, in a preferred embodiment, this is accomplished by forcing a consistent timing relationship between the injection event, the forced transfer operations during which pressure control is active, the mechanical position of the delivery pump pistons, and the start and subsequent gradient delivery. This enhances chromatographic performance related to retention time and area reproducibility.

Having described the operational relationship and interplay between the SDS 30 and injector valve 37, the elements of the SDS 30 will now be described. Each pump 32 and 34 comprises a primary pumping actuator 12 and an accumulator pumping actuator 14 that are structured and arranged in series. The primary pumping actuator 12 includes a primary chamber 12a and a reciprocating primary piston 12b. The accumulator pumping actuator 14 also includes an accumulator chamber 14a and a reciprocating accumulator piston 14b.

In a preferred embodiment, each primary pumping actuator 12 is disposed in fluid communication with a solvent source 31, upstream of the accumulator pumping actuator 14. Preferably, the outlet of the primary chamber 12a is in fluid communication with the accumulator chamber 14a. More preferably, each accumulator pumping actuator 14 is structured and arranged to be in fluid communication with the fluid stream of the SDS 30 via a flow-combining device 33, e.g., a T-section, and injector 37.

The primary pistons 12b perform all of the thermodynamic fluid work. More specifically, each primary piston 12b aspirates solvent from the solvent source 31; compresses the solvent to a desired pressure, e.g., a system operating pressure, and delivers the compressed solvent to the associated accumulator chamber 14b. The primary chambers 12a provide a discrete volume for holding the solvent during intake and during compression while off line. The accumulator chambers 14a also provide a discrete volume for holding the compressed solvent during flow delivery to the system (injector 37) while the primary actuators intake and compress for the next cycle.

Preferably, a passive check valve 11 of a type that is well-known to the art is disposed between the primary chamber 12a and the solvent source 31. In the closed position, the primary check valve 11 isolates the primary chamber 12a from the solvent source 31, preventing solvent from flowing back into the solvent source 31 while it is being compressed in the chamber 12a and delivered by the primary piston 12b. In the open position, the primary check valve 11 provides a fluid connection between the solvent source 31 and the primary chamber 12a for the purpose of re-filling the captive volume of the primary chamber 12b.

More preferably, a pressure transducer 17 of a type that is well-known to the art is disposed at or near the outlet of the primary chamber 12a. The pressure transducer 17 measures the pressure of the compressed solvent contained within the primary chamber 12a and transmits this pressure measurement in the form of a signal to a control device (not shown).

Similarly, in a preferred embodiment, a passive check valve 13 is disposed at the inlet of the accumulator chamber 14a. In the closed position, the accumulator check valve 13 isolates the accumulator chamber 14a from the primary chamber 12a, preventing compressed solvent in the accumulator chamber 14a from flowing back into the primary chamber 12a when solvent is being delivered by the accumulator piston 14b to the fluid stream of the SDS 30. In the open position, the accumulator check valve 13 provides a fluid connection between the primary chamber 12a, the accumulator chamber 14a, and the column 70 for the purpose of re-filling the captive volume of the accumulator chamber 14b and "over-delivering" solvent to the column 70.

A pressure transducer 19 is disposed at the outlet of the accumulator chamber 14a. The pressure transducer 19 measures the pressure of the delivery solvent in the accumulator chamber 14a and transmits this pressure to a controller (not shown). Preferably, the pressure measured by the pressure transducer 19 represents the operating pressure of the SDS 30.

The means for controlling the timing and operation of the pumps 32 and 34 will now be described. The primary piston 12b and accumulator piston 14b of each pump 32 and 34 are independently controlled by a control device or "controller", e.g., a processor, microprocessor (not shown), and the like. Preferably, control of the pistons 12b and 14b is exercised using pressure measurements received by the control device from the pressure transducers 17 and 19 and a control algorithm (not shown) that is provided for that purpose.

A further description of the pumps 32 and 34 and an explanation of how the pump components inter-relate are provided in the discussion of the timing diagram stages below. Moreover, preferred methods of providing active pressure control of the solvents to be introduced into the fluid stream of the SDS 30; of synchronizing the accumulator piston 14b and synchronizing the pumps 32 and 34; of providing a "forced transfer" of compressed solvent; and of introducing, i.e., injecting the analyte sample(s) into the fluid stream of the SDS 30 will also be described below.

Some of the problems addressed by the present invention include the temperature increase, known as adiabatic heating, and the resultant pressure decay, referred to as "cusping", which typically occur during a transfer operation. More specifically, the temperature increase creates an error in the pressure of the compressed solvent, because, at the time of compression, the solvent temperature is higher than the delivery temperature that the solvent will eventually have, i.e., the operating temperature of the system 15. Moreover, temperature gained due to an increase in pressure of the primary piston 12b is subsequently lost to the solvent surroundings and to the SDS 30 once the primary piston 12b starts delivering solvent. The loss rate depends on, inter alia, the relative mass and thermal conductivity of the compressed solvent and the surroundings.

Additionally, once the solvent is compressed to the desired delivery pressure, i.e., the system operating pressure, prior to a transfer operation, the resulting pressure starts to decay as its compression-induced increased temperature starts to equilibrate to the system operating temperature. The compressed solvent pressure eventually settles at a value below the intended system operating pressure, which creates a deficit in delivered flow when the primary piston 12b starts delivering to the fluid stream of the SDS 30. Preferably, to rectify this cusping effect, active pressure control is provided during a transfer operation. More preferably, active pressure control is provided with some time overlapping prior to and for a short period after the transfer operation. This is accomplished by forcing a consistent timing relationship between the injection event, the mechanical position of the delivery pump pistons; i.e., forced transfer operations, and the start and subsequent gradient delivery.

Figure 3:
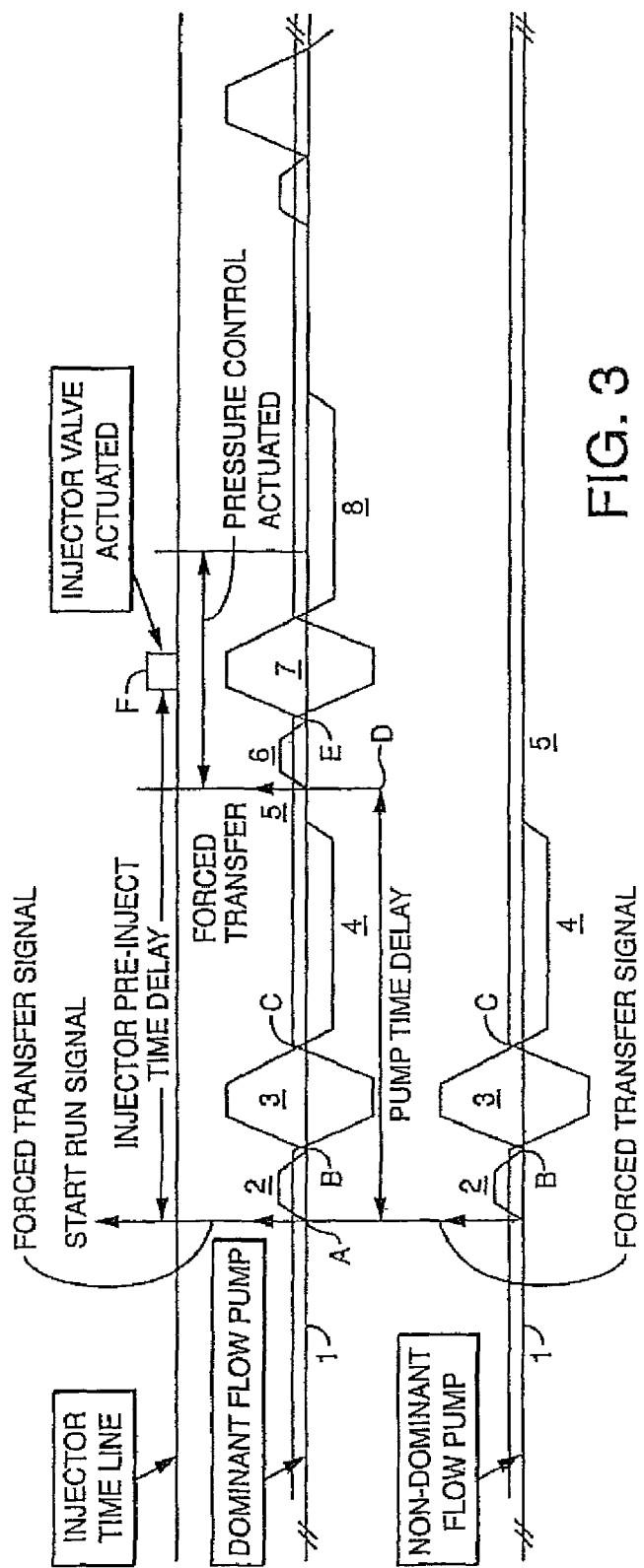
FIG. 3 is an illustrative embodiment of pump-injector synchronization timing diagram in accordance with the present invention.

Referring to FIG. 3, the various stages for providing active pressure control by forcing the pump transfer in relation to injection of the sample into the fluid stream of an SDS 30 from two or more pumps 32 and 34 will now be described. FIG. 3 depicts a timing diagram for synchronization of the pumps 32 and 34 and the injector 37. More specifically, the figure depicts timing relationships for the "dominant flow" pump and "non-dominant flow" pump, whereby each pump 32 and 34—or a plurality of pumps—can play either role.

For the purpose of this specification, the "dominant flow pump" refers to the pump that delivers the greater proportional share of solvent at the starting condition of the gradient method. Customarily, the "dominant flow pump" provides the weaker or aqueous solvent. In contrast, the "non-dominant flow pump" refers to the pump that delivers the lesser proportional share of the stronger solvent at the starting condition of the gradient method. Preferably, only the "dominant flow pump" actively participates with the forced transfer during an injection event of the analyte sample.

At the start of each injection run, the SDS 30 is set at the flow rate and solvent composition prescribed by the initial conditions of the sample-run gradient method. The system controller inspects the initial flow rates of both pumps 32 and 34 to choose which pump to play the role as the "dominant flow pump".

The reason for this is due to the nature of high-pressure mixing and correction of the inject pressure disturbance, which involves an "over-delivery" of solvent during active pressure control. However, "over-delivery" of one pump can have a deleterious effect on repeatable HPLC performance, because "over-delivery" upsets the starting composition of the analyte sample during injection of the same. The inventors of the present invention have discovered that less composition disturbance ensues when just one of the pumps, i.e., the "dominant flow pump", provides active pressure control during an injection event. This avoids possible interaction between the two pressure controllers by forcing a transfer to both pumps 32 and 34 prior to the injection event; then forcing a transfer to only the "dominant flow pump" during the injection event.

At some point A, the autosampler at the injector 37 has prepared the analyte sample for introduction, i.e., injection, into the fluid stream of the SDS 30 and has reached the stage where the sample loop is loaded and injection of the analyte sample is imminent. When the autosampler has reached this stage, the autosampler automatically transmits a "start run" signal to the SDS control device. This signal causes the control device to execute a series of forced transfers on both pumps 32 and 34. Preferably, to allow for pump synchronization, the autosampler transmits the "start run" signal at some predetermined, fixed time period, i.e., the "injector pre-inject time delay", prior to activating the injector valve 37 (point F). More preferably, the injector pre-inject time delay is sufficiently large to enable the SDS 30 to execute the sequence of operations (stages 2 to 7 described in greater detail below) to bring the appropriate pump 32 or 34, i.e., preferably the "dominant flow" pump, into active pressure control at the time of injection in stage 7.

When the control device of the SDS 30 receives the "start run" signal from the autosampler, it, in turn, signals both the "dominant flow" and the "non-dominant flow" pumps to begin their initial, or first, forced-transfer operation. Preferably, this step brings both pumps 32 and 34 into a consistent, i.e., uniform, state and, further, accomplishes one of the main objectives of the invention: to synchronize the mechanical phase of both pumps 32 and 34 during the analyte sample injection event.

Specifically, at the outset of forced-transfer, with respect to the "dominant flow" and "non-dominant flow" pumps, in stage 2, the primary pistons 12b perform their compression or forward stroke phase as soon as the intake stage of the current pump cycle is completed. The compression causes check valves 11 to close, isolating the primary chambers 12a from the solvent sources 31. With the primary check valves 11 closed, the control device causes the primary piston 12b of each pump 32 or 34 to compress the solvent that is stored (at rest) in the primary chamber 12a.

At the completion of stage 2 at point B, primary pistons 12b have completed their compression stroke, compressing the solvent in the primary chambers 12a. Once the solvents in the primary chambers 12a of each pump 32 and 34 have attained their designated or desired level of compression at the end of stage 2, the pressure of the solvents and the additional force of the primary pistons 12b cause the accumulator check valves 13 to open, establishing a fluid connection between the accumulator chambers 14a and the primary chambers 12a. Consequently, in stage 3; i.e., transfer operation, the primary pistons 12b of each pump 32 and 34 transfer or deliver compressed solvent to re-fill the accumulator chambers 14a, and the accumulator pistons 14b intake the compressed solvent.

During the forward stroke in stage 3, the primary pistons 12b actually "over-deliver" compressed solvent to the accumulator chambers 14a to maintain steady flow delivery to the fluid stream 52 of the SDS 30 while the accumulator piston 14b intakes. Because a forced transfer will typically occur before the accumulator chambers 14a have emptied their entire contents, an adjustment is made in stage 3 to the net primary delivery displacement so that the accumulator pistons 14b intake only the amount of compressed solvent necessary to replenish their normal stroke capacity.

At the end of stage 3 at point C, transfer is completed, which is to say that the primary pistons 12b have completed their delivery or re-filling of the accumulator chambers 14a. Simultaneously or substantially simultaneously, when the primary pistons 12b have completed their transfer operation, the accumulator pistons 14b begin delivering compressed solvent from the accumulator chambers 14a to the fluid stream 52 of the SDS 30 at the set flow rate for the next pump cycle.

At point C, the control device then commences primary intake in stage 4. As the primary pistons 12b begin to intake from the solvent source 31, the residual compressed solvent captive in the primary chamber 12a begins to decompress with the progressive withdrawal of the primary pistons 12b. This initial decompression causes the accumulator check valve 13 to close automatically, again isolating the accumulator chambers 14a from the primary chambers 12a. When the decompressing pressures in the primary chambers 12a reach atmospheric pressure, the primary check valves 11 open automatically, establishing fluid connections between the primary chambers 12a and the solvent sources 31. Thus, shortly after point C and during stage 4, the primary pistons 12b begin to aspirate or intake new solvent into the primary chambers 12a of the pumps 32 and 34.

Stage 4 is completed when the primary pistons 12b have completed their intake strokes. This transitions both pumps 32 and 34 to stage 5, where they await the next compress and transfer phase of their pump cycle.

At this stage, the SDS controller initiates a second forced transfer operation of the "dominant flow" pump only. Specifically, when a pre-designated time delay, i.e., the 'Pump Time Delay' in FIG. 3, expires after initiation and receipt of the 'Run Start' signal, the controller initiates a second forced transfer to the "dominant flow" pump at time D. The time relationship between the two time delays of the autosampler 37 and pump 32 and 34 are fixed to ensure that the second forced transfer (stage 7) of the "dominant flow" pump overlaps the injection event F on the injector time line. As a result, only the "dominant flow" pump—through this second forced transfer operation associated with its active pressure control—provides the necessary corrective flow to null or counter the injector pressure disturbance.

Stages 6, 7, and 8 of the second forced-transfer operation, which stages collectively define an "active pressure control" phase, are virtually identical to, respectively, stages 2, 3, and 4 of the first forced-transfer operation. Stages 6, 7, and 8, however, differ from stages 2, 3, and 4 in that active pressure control only applies to the "dominant flow" pump. In addition, the SDS controller extends the active pressure control time interval of the second forced-transfer to ensure adequate coverage, i.e., overlap, of the injection operation F. Indeed, as shown in FIG. 3, the "non-dominant flow" pump (at the bottom of the figure) will not require a transfer until well beyond injection event F. As a result, transfer and pump synchronization associated with the "non-dominant flow" pump have been completed before the analyte sample injection sequence, which prevents disruption of the gradient composition.

At some point F during the active pressure control phase, the autosampler signals the injector valve 37 to introduce, i.e., inject, the analyte sample from the sample loop 65 into the fluid stream of the SDS 30. Preferably, the duration of the active pressure control phase overlaps the injection event. In this manner, some portion of the second forced-transfer operation coincides with the switching of the injector valve 37 while pressure control is active during the pressure drop disturbance caused by the uncompressed analyte sample in the sample loop 65 being introduced into the fluid stream 52 of the SDS 30. Accordingly, active pressure control is provided by the "dominant flow" pump only, which will produce the least composition disturbance in the fluid stream 52.

Figure 4A:
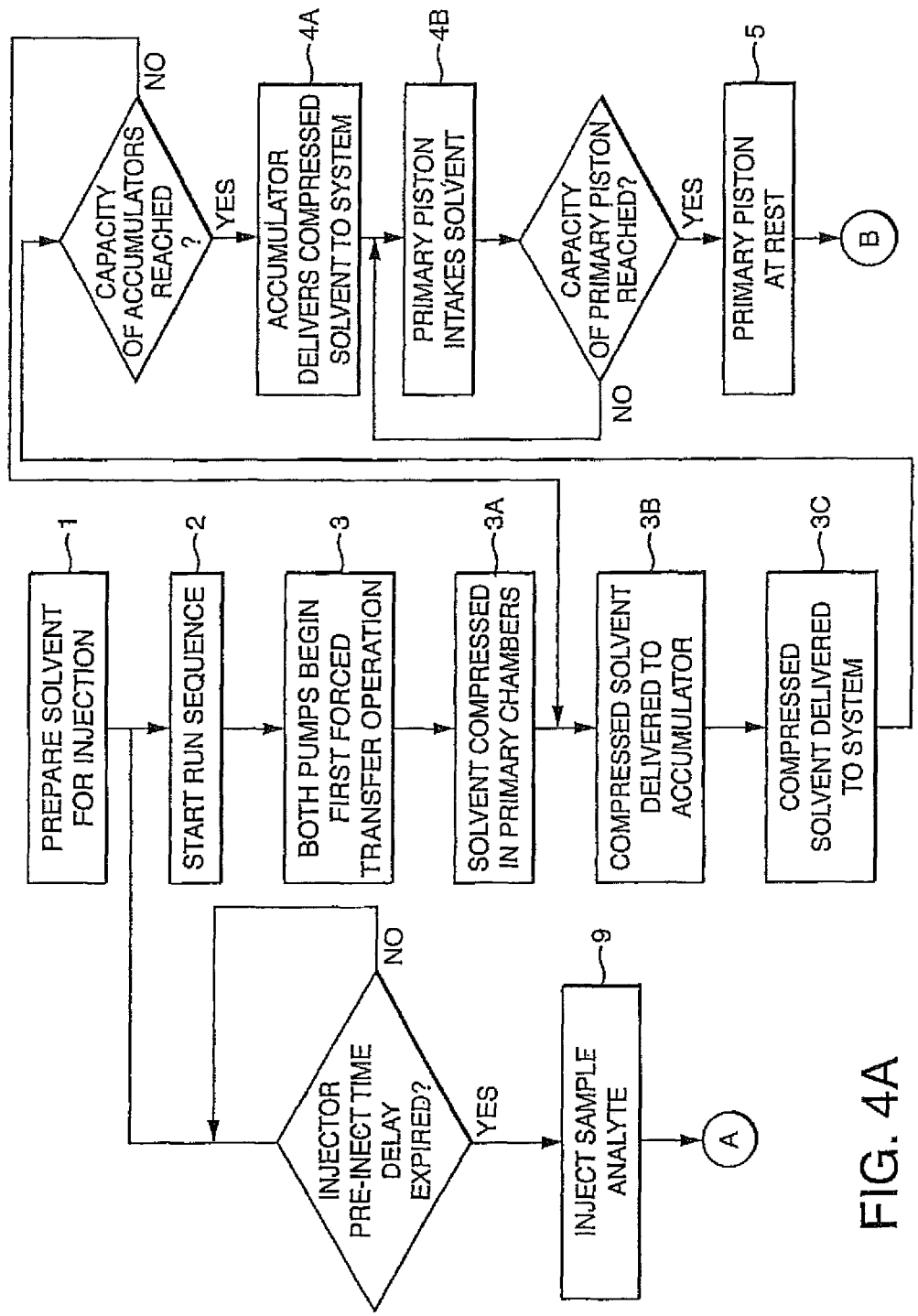
FIGS. 4A and 4B is a flow diagram showing an illustrative embodiment of a method of providing active pressure control to a system for controlling introduction of an analyte sample at a first pressure into a solvent fluid stream at a higher pressure.
Figure 4B:
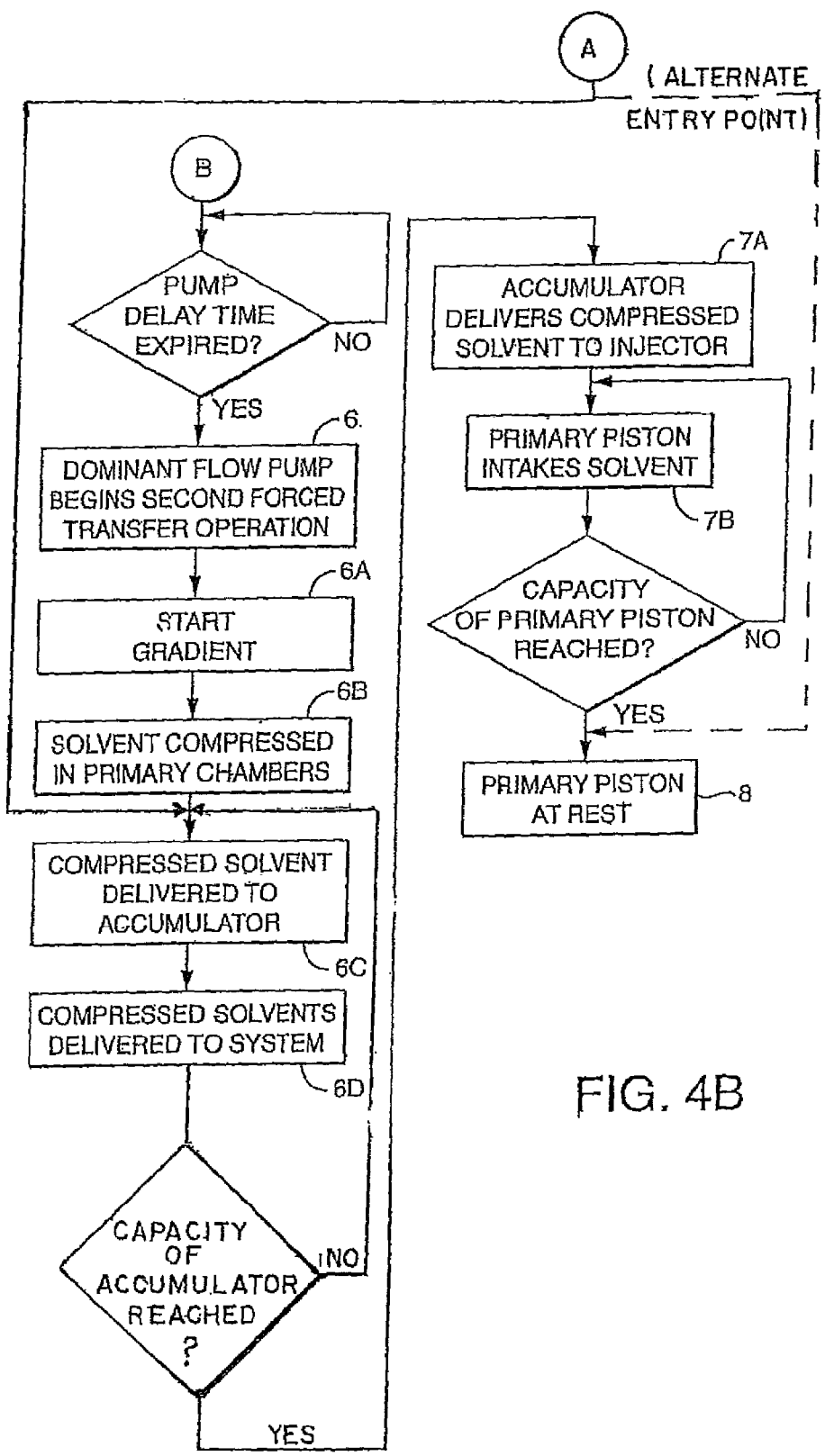

Referring to FIGS. 4A and 4B, methods of providing active pressure control and providing multiple forced-transfers of a plurality of solvents to a fluid stream of an SDS will now be described. The sequence begins when sample injector or the autosampler prepares the analyte samples for introduction, e.g., injection, into the fluid stream of the SDS (STEP 1). At this time, the SDS has prepared for the run by delivering solvent flow and composition at the initial starting conditions specified in the run method.

In a preferred embodiment, the analyte sample in the autosampler reaches a state whereby the sample is ready for introduction into the fluid stream of the SDS and such introduction is imminent. At this time, the injector valve is in the load state. With the analyte sample ready for immediate injection into the fluid stream, more preferably, the autosampler signals the control device to start the next run sequence (STEP 2).

In one aspect of the present invention, the autosampler transmits the trigger signal at a first desired, fixed time delay prior to activating the injector valve, through which the analyte sample is introduced into the fluid stream of the SDS. More preferably, the autosampler transmits a trigger signal sufficiently advanced in time for the SDS to execute a sequence of operations that brings the appropriate pump of the SDS into active pressure control at the time, i.e., the instant, of injection. Transmitting the trigger signal before activating the injector valve allows synchronization of the pumps.

Accordingly, the control device signals the "dominant flow" and "non-dominant flow" pumps to begin a first forced-transfer operation (STEP 3). In a preferred embodiment, both pumps reach a consistent state to synchronize flow delivery of solvents by both pumps. Specifically, the primary pistons of each pumps first compress the solvent contained in the corresponding piston chambers (STEP 3A) then the primary pumps deliver the compressed solvent to the corresponding accumulator chambers (STEP 3B) and, further, deliver compressed solvent to the system (STEP 3C).

Once the capacity of each of the accumulator pistons is reached, the accumulator pistons deliver compressed solvent from the accumulator chambers to the injector (STEP 4A). Simultaneously, the primary pistons stop delivering solvent to their corresponding accumulator chambers and to the injector and begin intaking more solvent from the solvent source (STEP 4B). Once the capacities of the primary chambers or the primary pumps are reached, the primary pistons are in an at-rest state (STEP 5), which is to say that, the primary pistons are neither intaking nor delivering compressed solvent.

Preferably, after a pre-determined period of time, i.e., the "pump time delay", the control device signals the "dominant flow" pump to begin a second forced-transfer operation (STEP 6), i.e., an "active pressure control" process, and pumps 32 and 34 start the run gradient (STEP 6A). Specifically, the primary piston of the "dominant flow" pump compresses the solvent in the primary chamber (STEP 6B) then delivers the compressed solvent concurrently to the accumulator chamber of the "dominant flow" pump (STEP 6C) and to the system (STEP 6D).

Once the capacity of the accumulator chamber of the "dominant flow" pump is reached, the accumulator piston of the "dominant flow" pump delivers compressed solvent to the injector (STEP 7A). Simultaneously, the primary piston of the "dominant flow" pump stops delivering solvent to the accumulator chamber and to the injector and begins intaking more solvent from the solvent source (STEP 7B).

Once the capacity of the primary piston of the "dominant flow" pump is reached, the primary piston is again returned to an at-rest state (STEP 8), which is to say that, the primary piston is neither intaking nor delivering solvent. Throughout this second forced-transfer operation, the "non-dominant flow pump" primary actuator remains in an at-rest state.

At some point during the second forced-transfer operation, or, more specifically, after a pre-determined period of time from the 'start run' signal, i.e., the "injector pre-inject time delay", the control device activates the injector valve and analyte sample captive within the sample loop is introduced into the fluid stream of the SDS (STEP 9). Preferably, the timing of the two fixed, time delays is such that the pressure control window of the second forced-transfer operation overlaps the analyte sample injection event. More preferably, the SDS commands the "dominant flow" pump to extend the pressure control window for a minimum duration that is necessary for adequate coverage of the injection disturbance of sample introduction. As a result, the "non-dominant flow" pump executes its transfer operation and pressure control before the injection window, which prevents disruption of the solvent gradient composition. Preferably, the injection step takes place prior to completion of the subsequent cycle of active pressure control process STEPS 6B to 8. After the injector has been activated (STEP 9), the primary chamber of the "dominant flow" pump requires refilling STEP 7B, after which a normal pump cycle resumes.

For illustrative purposes only, the injection step (STEP 9) has been shown generally to occur between STEPS 6B and 8, i.e., within the subsequent cycle of "active pressure control" steps following the two forced-transfer operations. The invention, however, is not to be interpreted or construed as being limited to the injection step STEP 9 taking place only at any particular location within these steps. The requirement is that "active pressure control" occurs during an injection event.

While the subject invention has been described with respect to preferred embodiments, those skilled in the art will readily appreciate that various changes and/or modifications can be made to the invention without departing from the spirit or scope of the invention.

What is claimed is:

1. A binary solvent delivery device for controlling introduction of an analyte sample at a first pressure into a fluid stream at a higher second pressure, wherein the fluid stream is that of a system for analyzing the analyte sample and introduction occurs during a forced transfer operation involving an autosample injector valve and a plurality of pumping actuators having one dominant flow pumping actuator and at least one non-dominant flow pumping actuator for creating a pressurized stream for the autosample injector valve into which the autosample injector introduces the analyte sample so that the binary solvent device minimizes an expectant pressure drop that occurs when the pressurized stream containing the analyte sample is introduced into said fluid stream by the autosample injector valve, the device comprising:
a first signaling means for providing a first start run signal to the plurality of pumping actuators;
memory for storing a pre-determined injector pre-inject time delay and a pre-determined pump time delay;
a time-measuring means for measuring a first amount of time starting upon sending the first start run signal and a second amount of time starting upon sending the first start run signal;
a comparator for comparing the first and second amounts of time, respectively, to the pre-determined injector pre-inject time delay and the pre-determined pump time delay stored in memory;
a second signaling means for providing a second signal to the dominant pumping actuator of the plurality of pumping actuators when the second amount of time equals the pre-determined pump time delay; and
a third signaling means for providing a third signal to the autosample injector valve through which the analyte sample is introduced into the fluid stream of the system when the first amount of time equals the pre-determined injector pre-inject time delay;
wherein the first start run signal causes the dominant flow pumping actuator and the non-dominant flow pumping actuator to perform a first forced transfer operation concurrently and the second signal causes only the dominant flow pumping actuator to perform a second forced transfer operation.

2. The device as recited in claim 1, further comprising means to synchronize a mechanical phase of each pumping actuator with at least one of an injection sequence and a start of a gradient run to enhance retention time reproducibility between a plurality of injection runs.

3. The device as recited in claim 2, wherein the first signaling means, the time-measuring means, the comparator, the second signaling means, the third signaling means, and the means to synchronize are a controller.

4. The device as recited in claim 1, wherein the second forced transfer operation overlaps an injection event occurring when the analyte sample is introduced into the fluid stream of the system for analyzing the analyte sample.

5. The device as recited in claim 1, wherein the device is structured and arranged to provide active pressure control during each forced transfer operation to minimize disturbance in the fluid stream during introduction of the analyte sample.

6. A computer-readable medium whose contents cause a control device to perform a method for controlling introduction of an analyte sample at a first pressure into a fluid stream at a higher second pressure, wherein the fluid stream is that of a system for analyzing the analyte sample, during a forced transfer operation involving an autosample injector valve and a plurality of pumping actuators having one dominant flow pumping actuator and at least one non-dominant flow pumping actuator for creating a pressurized stream for the autosample injector valve into which the autosample injector valve introduces the analyte sample in order to minimize an expectant pressure drop that occurs when the analyte sample is introduced into the fluid stream by the autosample injector valve, the piece of software having an algorithm that comprises:
providing a first start run signal to a plurality of pumps;
storing a pre-determined injector pre-inject time delay and a pre-determined pump time delay in memory;
measuring a first amount time starting upon sending the first start run signal and a second amount of time starting upon sending the first start run signal;
comparing the first and second amounts of time, respectively, to the pre-determined injector pre-inject time delay and the pre-determined pump time delay stored in memory;
providing a second signal to the dominant flow pumping actuator of the plurality of pumping actuators when the second amount of time equals the pre-determined pump time delay; and
providing a third signal to the autosample injector valve through which the analyte sample is introduced into the fluid stream of the system when the first amount of time equals the pre-determined injector pre-inject time delay.

7. The computer-readable medium as recited in claim 6, wherein the algorithm ensures that the second forced transfer operation overlaps an injection event occurring when the analyte sample is introduced into the fluid stream of the system.

8. The computer-readable medium as recited in claim 6, wherein the algorithm provides active pressure control during at least one forced transfer operation to minimize disturbance to the fluid stream during the injection event.

9. The computer-readable medium as recited in claim 6, wherein the software algorithm further includes synchronizing a mechanical phase of each pumping actuator with at least one of an injection sequence and a start of a gradient run to enhance retention time reproducibility between a plurality of injection runs.

10. A system for controlling introduction of an analyte sample at a first pressure during active pressure control of a dominant flow pumping actuator, to minimize an expectant pressure drop that occurs when the analyte sample is introduced by an injector valve into a fluid stream at a second higher pressure of a system for analyzing said analyte sample, the control system comprising:

a control device for receiving pressure measurements and for providing signals for active pressure control;

a plurality of pumping actuators to provide high-pressure mixing of gradients of a plurality of solvents into a fluid stream of the system, wherein each of the plurality of pumping actuators is in fluid communication with a flow-combining device, and wherein a dominant flow pumping actuator that is further in fluid communication with a first solvent source; and one or more non-dominant flow pumping actuators that are further in fluid communication with a one or more solvent sources; and an autosampler that is structured and arranged at the injector valve, to provide signals to the control device.

11. The system as recited in claim 10, wherein each of the dominant flow pumping actuator and one or more non-dominant flow pumping actuator includes:

a primary pumping actuator having a chamber and a piston that is disposed downstream of and in fluid communication with a solvent source; and an accumulator pumping actuator having a chamber and a piston that is disposed downstream of and in series with the primary pumping actuator and upstream of an injector.

12. The system as recited in claim 11, wherein the system further includes a check valve that is disposed between the primary pumping actuator and the solvent source, wherein in an open position, the check valve provides fluid communication between the primary pumping actuator and the solvent source so that the piston can intake solvent from the solvent source and store said solvent in the chamber, and in a closed position, the check valve isolates the primary pumping actuator from the solvent source to prevent solvent in said chamber from flowing back into said solvent source when the piston of said primary pumping actuator compresses said solvent in said chamber or delivers said solvent to the chamber of the accumulator pumping actuator.

13. The system as recited in claim 11, wherein the system further includes a check valve that is disposed between the primary pumping actuator and the accumulator pumping actuator, wherein in an open position, the check valve provides fluid communication between the chamber of the primary pumping actuator and the chamber of the accumulator pumping actuator so that the piston of the primary pumping actuator can deliver solvent to said chamber of said accumulator pumping actuator, and in a closed position, the check valve isolates the chamber of the accumulator pumping actuator from the primary pumping actuator to prevent solvent in said chamber of said accumulator pumping actuator from flowing back into the chamber of said primary pumping actuator when the piston of said accumulator pumping actuator delivers said solvent to the system.

14. The system as recited in claim 11, wherein one or more of the chambers includes a pressure transducer that is disposed at an outlet thereof for providing pressure measurements to the device controller.

15. The system as recited in claim 11, wherein the system is structured and arranged so that during a first forced transfer operation, the primary pistons of the dominant flow pumping actuator and the non-dominant flow pumping actuator compress their aspirated solvent; re-fill their associated accumulator chambers; and, further, deliver compressed solvent to the injector.

16. The system as recited in claim 15, wherein the autosampler provides a first signal to the control device to initiate the first forced transfer operation.

17. The system as recited in claim 14, wherein the autosampler provides the first signal to the control device at some pre-determined, fixed time period prior to activating the injector to enable pump synchronization.

18. The system as recited in claim 17, wherein the pre-determined, fixed time period is sufficiently large to bring one of the dominant flow pumping actuator and the non-dominant flow pumping actuator into active pressure control coincident with introducing the analyte sample into the fluid stream.

19. The system as recited in claim 11, wherein the system is structured and arranged so that during a second forced transfer operation, the primary piston of the dominant flow pumping actuator compresses its aspirated solvent; re-fills its associated accumulator chamber; and, further, delivers compressed solvent to the injector.

20. The system as recited in claim 19, wherein the autosampler provides a second signal to the control device to initiate the second forced transfer operation.

21. The system as recited in claim 20, wherein the autosampler provides the second signal to the control device at some pre-determined, fixed time period prior to activating the injector to enable pump synchronization.

22. The system as recited in claim 21, wherein the pre-determined, fixed time period is sufficiently large to bring the dominant flow pumping actuator into active pressure control coincident with introducing the analyte sample into the fluid stream.

23. The system as recited in claim 19, wherein the system for analyzing said analyte sample is a high-performance liquid chromatography device.

24. The system as recited in claim 11, wherein the system is structured and arranged so that active pressure control ensures that there is no overlap between a control period of the dominant flow pumping actuator and a control period of the non-dominant pump during a second forced transfer operation.

25. The system as recited in claim 24, wherein overlap between the control periods of the dominant flow pumping actuator and the non-dominant flow pumping actuator is avoided by advancing the control period of one of said pumping actuators having a longer pump cycle than the other of said pumping actuators.

26. The system as recited in claim 24, wherein during active pressure control, the dominant flow pumping actuator provides a greater share of solvent at the starting condition of a system run.

27. The system as recited in claim 26, wherein the dominant flow pumping actuator provides either an aqueous solvent or a solvent that is weaker that the solvent provided by the non-dominant flow pumping actuator.

28. The system as recited in claim 10, wherein the flow-combining device is a T-section.

29. The system as recited in claim 10, wherein the flow-combining device is a mixer that can blend the two or more solvents prior to their introduction into the fluid stream.

30. A method of providing active pressure control to a system for controlling introduction of an analyte sample at a first pressure into a solvent fluid stream at a second higher pressure from one of a plurality of pumping actuators to minimize an expectant pressure drop that occurs when the analyte sample at a lower pressure is introduced into a system for analyzing said analyte sample, the method comprising:

preparing the analyte sample for introduction into the fluid stream;

initiating a first forced transfer operation upon starting a run, wherein the first forced transfer operation includes at least one of synchronizing a delivery stroke of a plurality of accumulator actuator pistons among the plurality of pumping actuators and synchronizing a mechanical phase of the plurality of accumulator actuator pistons;

initiating a second forced pressure control transfer operation after a pump delay period from starting the run, wherein the second forced transfer operation is applied only to the dominant flow pumping actuator while the non-dominant primary pumping actuator is in its rest state; and activating an injector valve to introduce said analyte sample into the fluid stream of the system after an injector pre-inject delay period from starting the run.

31. The method as recited in claim 30, wherein the first forced transfer operation is initiated at a first, pre-determined, fixed time delay prior to activating the injector valve.

32. The method as recited in claim 30, wherein the first forced transfer operation is initiated prior to the injection step to synchronize the dominant flow pumping actuator with the non-dominant flow pumping actuator.

33. The method as recited in claim 30, wherein the step of initiating a second forced transfer operation overlaps the step of activating the injector valve to introduce the analyte sample into the fluid stream of the system.

34. A device for controlling introduction of an analyte sample at a first pressure into a fluid stream at a higher second pressure, wherein the fluid stream is that of a system for analyzing the analyte sample, during a forced transfer operation involving an injector valve and a plurality of pumping actuators having one dominant flow pumping actuator and at least one non-dominant flow pumping actuator for creating a pressurized stream for the injector valve into which the injector valve introduces the analyte sample so that the device minimizes an expectant pressure drop that occurs when the pressurized stream containing the analyte sample is introduced into the fluid stream of the system by the injector valve, the device comprising:

memory for storing a pre-determined injector pre-inject time delay and a pre-determined pump time delay;

a time-measuring means for measuring a first amount of time starting upon sending a first start run signal and a second amount of time starting upon sending the first start run signal;

a comparator for comparing the first and second amounts of time, respectively, to the pre-determined injector pre-inject time delay and the pre-determined pump time delay stored in memory; and a controller that:

provides the first start run signal to the plurality of pumps;

provides a second signal to the dominant pump of the plurality of pumps when the second amount of time equals the pre-determined pump time delay; and provides a third signal to an injector valve through which the analyte sample is introduced into the fluid stream of the system when the first amount of time equals the pre-determined injector pre-inject time delay.

35. The device as recited in claim 34, wherein the first signal causes the dominant flow pumping actuator and the non-dominant flow pumping actuator to perform a first forced transfer operation concurrently and the second signal causes only the dominant flow pumping actuator to perform a second forced transfer operation.

36. The device as recited in claim 34, wherein the device further comprising means to synchronize a mechanical phase of each pumping actuator with at least one of an injection sequence and a start of a gradient run to enhance retention time reproducibility between a plurality of injection runs.

37. The device as recited in claim 34, wherein the second forced transfer operation overlaps an injection event occurring when the analyte sample is introduced into the fluid stream of the system.

38. The device as recited in claim 34, wherein the device is structured and arranged to provide active pressure control during each forced transfer operation to minimize disturbance in the fluid stream during introduction of the analyte sample into said fluid stream.

39. The device as recited in claim 34, wherein the controller is the time-measuring means, the comparator, and the means to synchronize.

* * * * *